United States Patent
Van Egmond et al.

(10) Patent No.: US 7,626,067 B2
(45) Date of Patent: Dec. 1, 2009

(54) PROCESS FOR RECOVERING AND REUSING WATER IN AN OXYGENATE-TO-OLEFIN PROCESS

(75) Inventors: Cor F. Van Egmond, Pasadena, TX (US); Zhong Yi Ding, Wayne, NJ (US); James H. Beech, Jr., Kingwood, TX (US); Michael P. Nicoletti, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 666 days.

(21) Appl. No.: 10/870,185

(22) Filed: Jun. 17, 2004

(65) Prior Publication Data

US 2005/0065390 A1    Mar. 24, 2005

Related U.S. Application Data

(60) Provisional application No. 60/504,450, filed on Sep. 19, 2003.

(51) Int. Cl.
*C07C 1/00* (2006.01)
*B01J 29/06* (2006.01)
*C01B 39/00* (2006.01)

(52) U.S. Cl. ............... 585/640; 585/639; 585/809; 502/64; 502/77; 502/214; 502/232; 423/700

(58) Field of Classification Search ............... 585/639, 585/640, 809
See application file for complete search history.

(56) References Cited

U.S. PATENT DOCUMENTS

| | | | | |
|---|---|---|---|---|
| 4,387,263 | A | 6/1983 | Vogt et al. | 585/640 |
| 4,886,651 | A | 12/1989 | Patel et al. | 423/359 |
| 4,981,491 | A | 1/1991 | Harandi et al. | 44/448 |
| 5,028,400 | A | 7/1991 | Harandi et al. | 422/211 |
| 5,047,070 | A | 9/1991 | Harandi et al. | 44/446 |
| 5,430,219 | A | 7/1995 | Sanfilippo et al. | 585/659 |
| 5,599,955 | A | 2/1997 | Vora et al. | 549/525 |
| 5,817,906 | A | 10/1998 | Marker et al. | 585/640 |
| 6,121,504 | A | 9/2000 | Kuechler et al. | 585/640 |
| 6,403,854 | B1 | 6/2002 | Miller et al. | 585/638 |
| 6,459,009 | B1 | 10/2002 | Miller et al. | 585/809 |
| 6,495,609 | B1 | 12/2002 | Searle | 518/700 |

FOREIGN PATENT DOCUMENTS

| | | |
|---|---|---|
| EP | 0 933 345 | 8/1999 |
| WO | WO 99/55650 | 11/1999 |
| WO | WO 02/00579 | 1/2002 |

*Primary Examiner*—In Suk Bullock
(74) *Attorney, Agent, or Firm*—Kevin M. Faulkner; David M. Weisberg; Jaimes Sher

(57) ABSTRACT

The present invention is a process for cleaning and using byproduct water from an oxygenate to olefin process to satisfy the water requirement of the oxygenate to olefin process.

18 Claims, 2 Drawing Sheets

PROCESS FOR RECOVERING AND REUSING WATER IN AN OXYGENATE-TO-OLEFIN PROCESS

CROSS-REFERENCE TO RELATED APPLICATIONS

The present application claims the benefit of U.S. Provisional Application No. 60/504,450, filed Sep. 19, 2003, said application hereby incorporated by reference.

FIELD OF THE INVENTION

The present invention relates to conservation of water in an oxygenate-to-olefin process.

BACKGROUND OF THE INVENTION

Olefins are traditionally produced from petroleum feedstock by catalytic or steam cracking processes. These cracking processes, especially steam cracking, produce light olefins such as ethylene and/or propylene from a variety of hydrocarbon feedstock. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefins. This process is referred to as the oxygenate-to-olefin process. The preferred oxygenate for light olefin production is methanol. The process of converting methanol to olefins is called the methanol-to-olefins process.

There are numerous technologies available for producing oxygenates, and particularly methanol, including fermentation or reaction of synthesis gas derived from natural gas, petroleum liquids, carbonaceous materials including coal, recycled plastics, municipal waste or any other organic material. The most common process for producing methanol is a two-step process of converting natural gas to synthesis gas. Then, synthesis gas is converted to methanol.

Generally, the production of synthesis gas involves a combustion reaction of natural gas, mostly methane, and an oxygen source into hydrogen, carbon monoxide and/or carbon dioxide. Synthesis gas production processes are well known, and include conventional steam reforming, autothermal reforming or a combination thereof.

Synthesis gas is then processed into methanol. Specifically, the components of synthesis gas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol is then converted to olefins in a methanol-to-olefins process. The methanol-to-olefins reaction is highly exothermic and produces a large amount of water. Water often comprises more than one half of the total weight of the effluent stream. Consequently, the water must be removed by condensation in a quench device to isolate the olefin product.

U.S. Pat. No. 6,121,504 describes a quench apparatus for an oxygenate to olefins process as well as a process for using a quench apparatus. The process removes water from the effluent stream as well as some oxygenate feedstock such as methanol. When the water is quenched, a portion of the water is cooled and recycled to the quench tower as quench medium. Additionally, the quench bottoms stream is passed through heat exchangers as a heat source for the methanol feed. Otherwise, water is sent to wastewater treatment.

U.S. Pat. No. 6,403,854 describes a two stage solids wash and quench for use with the oxygenate conversion process where catalyst fines are removed from the effluent stream through a first quench stage. Water and methanol is removed from the effluent stream in a second quench stage. The quench bottoms from the first quench stage is withdrawn as an aqueous waste stream or drag stream and is sent to a water treatment zone. A portion of the water from the quench bottoms of the second stage is cooled and reused as a quench medium. Otherwise, water is sent to wastewater treatment.

It would be advantageous, particularly in arid climates, to be able to find a better use for byproduct water from a methanol to olefins plant than to dispose of it in wastewater treatment. The present invention satisfies these and other needs.

SUMMARY OF THE INVENTION

The present invention is a process for cleaning and using byproduct water from an oxygenate to olefin process to satisfy the water requirement of the oxygenate to olefin process.

In one embodiment, the invention is to a process for converting oxygenates to one or more olefin product streams, the process having a process water requirement, and the process comprising the steps of: (a) providing an oxygenate feed stream to an oxygenate to olefin reactor; (b) contacting the oxygenate feed stream in the oxygenate to olefin reactor with a molecular sieve catalyst under conditions effective to produce an effluent stream comprising one or more olefins and byproduct water; (c) recovering said one or more olefins in one or more olefin product streams; (d) recovering the byproduct water from the effluent stream in the form of process quality water; and (e) using about 25 wt. % or more of the byproduct water based upon the total weight of byproduct water for the process water requirement.

Optionally, step (c) has the process water requirement. Optionally, the effluent stream is entrained with catalyst fines and further comprises oxygenated hydrocarbons, wherein the process further comprises the step of: (f) removing oxygenated hydrocarbons and catalyst fines from the byproduct water, wherein steps (c), (d) and (f) result in process quality water.

In any embodiment, the effluent stream optionally comprises from about 30 wt. % to about 70 wt. % water, based upon the composition of the effluent stream. Additionally or alternatively, the effluent stream comprises from about 0.05 wt. % to about 5 wt. % alcohol based upon the composition of the effluent stream as the effluent stream leaves the reactor. Additionally or alternatively, the effluent stream comprises from about 0.01 wt. % to about 5 wt. % organic acids based upon the composition of the effluent stream as the effluent stream leaves the reactor. Additionally or alternatively, the effluent stream comprises about 5 wt. % or less aromatic compounds based upon the composition of the effluent stream as the effluent stream leaves the reactor. Additionally or alternatively, the effluent stream comprises about 0.3 wt. % or less nitrogen containing compounds, based upon the composition of the effluent stream. Additionally or alternatively, the effluent stream comprises about 0.3 wt. % or less sulfur containing compounds, based upon the composition of the effluent stream. Additionally or alternatively, the effluent stream comprises from about 0.3 wt. % or less halogen, based upon the composition of the effluent stream.

Preferably, step (c) comprises quenching the effluent stream to form a quenched effluent stream and a quench bottoms stream. Optionally, the quench bottoms stream comprises from about 0.05 wt. % to about 5 wt. % alcohol, about 5 wt. % or less catalyst fines, from about 0.01 wt. % to about 5 wt. % organic acids, about 5 wt. % or less aromatic compounds, about 0.1 wt. % or less nitrogen containing compounds, about 0.1 wt. % or less sulfur containing compounds, about 0.1 wt. % or less halogen containing compounds, and/or about 1 wt. % or less metal ion salts, based upon the composition of the quench bottoms stream as the quench bottoms stream leaves the quench device.

In any of these embodiments, the process quality water may comprise about 0.5 wt. % or less catalyst fines based upon the composition of the process quality water. Additionally or alternatively, the process quality water comprises about 0.1 wt. % or less alcohol, less than about 0.1 wt. % methanol, less than about 0.1 wt. % organic acids, and/or about 0.01 wt. % or less aromatic compounds, based upon the composition of the process quality water.

In one preferred embodiment, the step of (e) using, uses 30 wt. % or more of the byproduct water. Optionally, the step of (e) using, satisfies 30 wt. % or more of the water requirement from byproduct water.

In one embodiment, there is a process for converting oxygenates to one or more olefin product streams. The process comprises providing an oxygenate feed stream to an oxygenate to olefin reactor. The oxygenate feed stream is contacted in the oxygenate to olefin reactor with a molecular sieve catalyst under conditions effective to produce an effluent stream comprising one or more olefins and byproduct water. Byproduct water is water that is produced as a byproduct in the reaction that converts oxygenates to olefins. One or more olefins is recovered in one or more olefin product streams. The oxygenate to olefin process has a water requirement. By water requirement, it is meant, the amount of water consumed in an oxygenate to olefin process by steps or applications that consume water without recovering the water in the process. Next, the byproduct water is recovered from the effluent stream in the form of process quality water. Overall about 25 wt. % or more of the byproduct water is used based upon the total weight of byproduct water for the process water requirement.

In another embodiment, the invention is to a process for converting oxygenates to one or more olefin product streams. The process comprises the steps of providing an oxygenate feed stream to an oxygenate to olefin reactor. The oxygenate feed stream is contacted in the oxygenate to olefin reactor with a molecular sieve catalyst under conditions effective to produce an effluent stream comprising one or more olefins and byproduct water. The one or more olefins are recovered in one or more olefin product streams. The step of recovering has a process water requirement. The byproduct water is recovered from the effluent stream in the form of process quality water. About 25 wt. % or more of byproduct water is supplied for the process water requirement with byproduct water.

In one embodiment the invention is to a process for converting oxygenates to one or more olefin product streams, the process comprising the steps of: (a) providing an oxygenate feed stream to an oxygenate to olefin reactor; (b) contacting the oxygenate feed stream in the oxygenate to olefin reactor with a molecular sieve catalyst under conditions effective to produce an effluent stream comprising one or more olefins and byproduct water; (c) recovering said one or more olefins in one or more olefin product streams, the step of recovering having a process water requirement; (d) recovering the byproduct water from the effluent stream in the form of process quality water; and (e) supplying about 25 wt. % or more of byproduct water for process water requirement with byproduct water.

In another embodiment, the invention is to process for converting oxygenates to one or more olefin product streams, the process comprising the steps of: (a) providing an oxygenate feed stream to an oxygenate to olefin reactor; (b) contacting the oxygenate feed stream in the oxygenate to olefin reactor with a molecular sieve catalyst under conditions effective to produce an effluent stream comprising one or more olefins, oxygenated hydrocarbons and byproduct water, wherein the effluent stream is entrained with catalyst fines; (c) recovering one or more olefins into one or more olefin product streams, wherein the process having a process water requirement; (d) separating said byproduct water from the one or more olefins; (e) removing oxygenated hydrocarbons and catalyst fines from the byproduct water, wherein the steps of (c) recovering through (e) removing results in process quality water; and (f) using about 25 wt. % or more of the byproduct water based upon the total weight of byproduct water to supply about 25 wt. % or more of the process water requirement.

In still another embodiment, about 25 wt. % or more of the byproduct water based upon the total weight of byproduct water supplies about 25 wt. % or more of the process water requirement.

DETAILED DESCRIPTION OF THE INVENTION

Introduction and Overview

Figure 1:
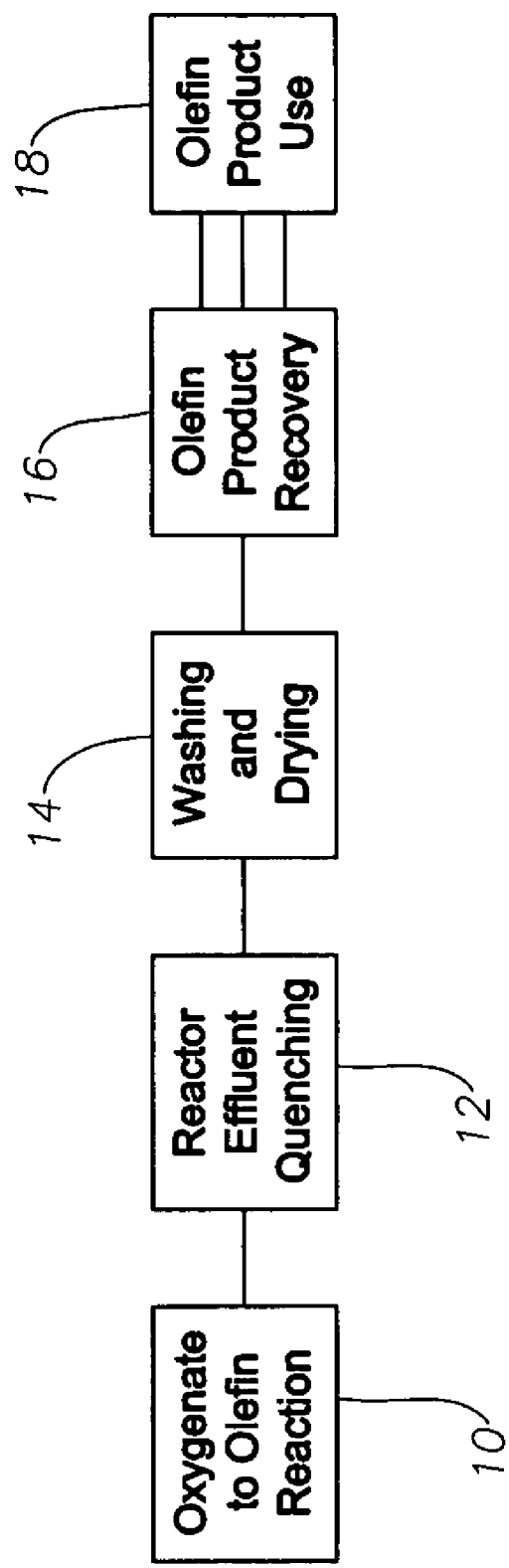
FIG. 1 illustrates the overall process of an oxygenate to olefins plant according to one embodiment of the present invention.

The present invention is directed to processes for recovering byproduct water from an oxygenate to olefins reaction system and using the byproduct water to satisfy a process water requirement in the reaction system. In one embodiment, the invention is to a process for preparing a quench bottoms stream for process feed water. To aid in the understanding of the present invention, a brief overview of the processing steps of producing and using one or more olefin products from an oxygenate feed stream is discussed with reference to FIG. 1. The oxygenate to olefin reactor 10 converts an oxygenate feed stream into an olefin product. The gaseous output stream of an oxygenate to olefin reactor 10 is defined as the effluent stream. The reactor effluent stream is particularly the gaseous output stream from the point it leaves the reactor 10 to the point it is quenched 12. The step of quenching 12 cools the effluent stream and removes water and catalyst fines from the effluent stream. The present invention relates to the treatment of catalyst fines in the step of quenching 12. According to one embodiment of the present invention, water is treated and reused as process water for any water requirements of an oxygenate to olefins plant including boiler feed water and cooling tower make-up. Optionally, or alternatively, process water is used as feed to a syngas reformer. Included in the step of quenching is optional compression of the effluent stream.

Optionally, the quenched effluent stream then undergoes a step of washing and drying 14 to produce a dried effluent stream. Washing the quenched effluent stream removes acid components in the effluent stream, such as carbon dioxide. Drying removes water that is saturated in the quenched effluent stream. Optionally, the washing and drying stage includes processing steps to remove additional oxygenates.

The dried effluent stream then undergoes a step of recovering the olefin products 16. Particularly, light olefins, i.e. ethylene and propylene, may be recovered in an acceptable grade of purity for a particular application. Thereafter the recovered olefin products may be used in various product applications 18. For example, the olefins may be used in a polymerization process to make polyolefin products. The present invention is an improvement to the process of making olefins from an oxygenate feed stream. Accordingly, the present invention including a more detailed discussion of each step in the manufacture and use of olefins from an oxygenate feed stream is discussed below.

The Oxygenate-to-Olefin Reaction

Figure 2:
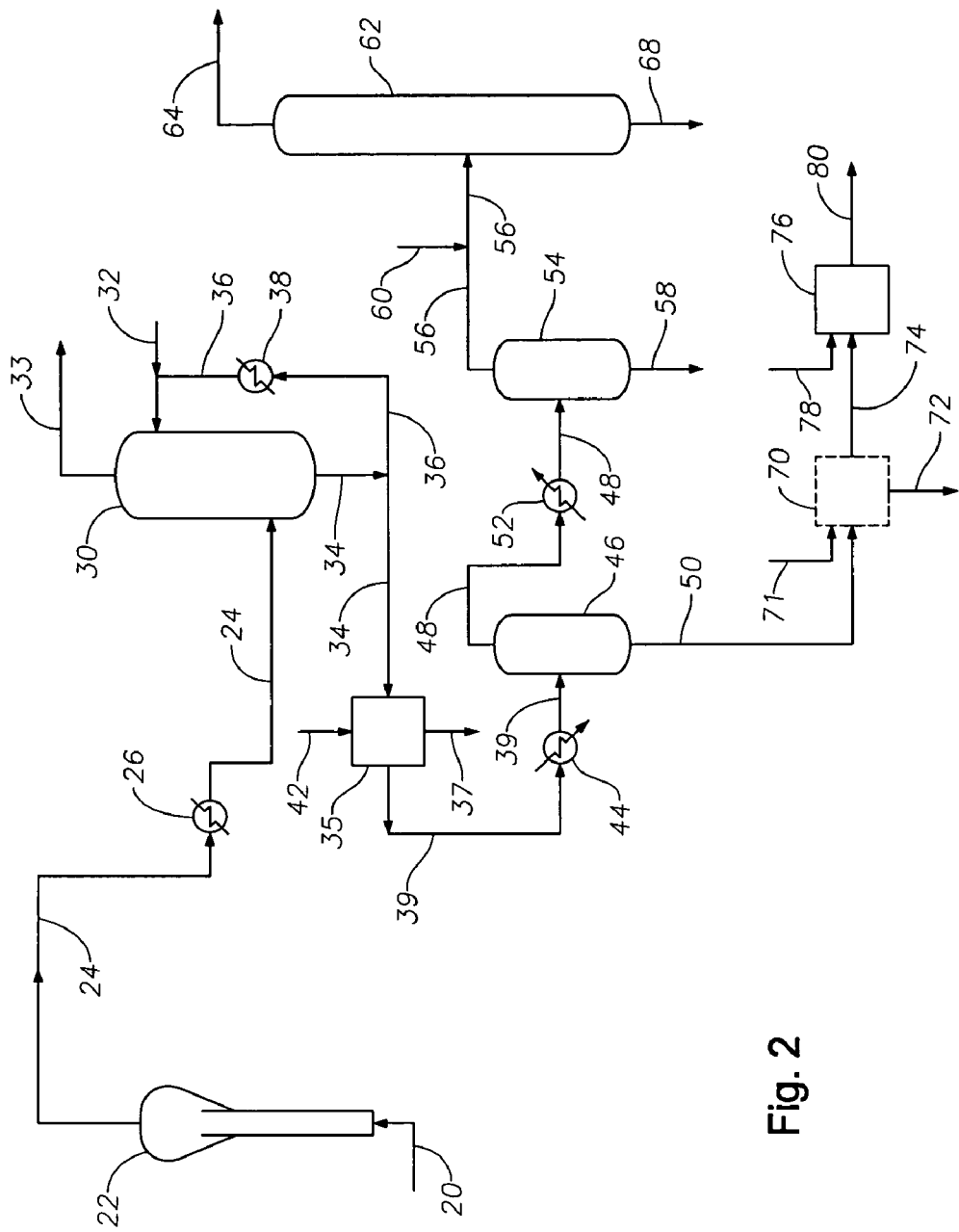
FIG. 2 illustrates a process for preparing process feed water for reuse in an oxygenate to olefin plant.

As shown in FIG. 2, an oxygenate feed stream is fed along line 20 into an oxygenate-to-olefin reactor 22 producing a reactor effluent stream that is withdrawn along line 24. The reactor 22 uses a catalyst, for example, a molecular sieve catalyst, made from a molecular sieve catalyst composition.

Molecular sieve catalysts are useful for conversion of a feed stream that contains one or more aliphatic-containing compounds. The one or more aliphatic-containing compounds are disclosed in PCT Publication Nos. WO 03/000412 and WO 03/000413, the contents of which are incorporated herein by reference.

In a preferred embodiment of the process of the invention, the feed stream is an oxygenate feed stream. Particularly, an oxygenate feed stream is a feed stream that comprises one or more organic compound(s) containing at least one oxygen atom. Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the oxygenate feed stream comprises oxygenates selected from one or more of methanol, ethanol, dimethyl ether, diethyl ether or a combination thereof, more preferably methanol and dimethyl ether, and most preferably methanol.

In one embodiment, the oxygenate feed stream is produced from an integrated process for producing oxygenates, particularly alcohols, from a hydrocarbon feedstock, preferably a hydrocarbon gas feedstock, more preferably methane and/or ethane. A method of preparing an alcohol feedstock is disclosed in PCT Publication Nos. WO 03/000412 and WO 03/000413, the contents of which are incorporated herein by reference. The methanol production process produces an oxygenate containing stream, or crude methanol, typically contains the alcohol product and various other components such as ethers, particularly dimethyl ether, ketones, aldehydes, dissolved gases such as hydrogen methane, carbon oxide and nitrogen, and fusel oil.

The oxygenate containing stream, crude methanol, in the preferred embodiment is passed through a well known purification processes, distillation, separation and fractionation, resulting in a purified oxygenate containing stream, for example, crude methanol, other subgrade methanol compositions, commercial Grade A methanol and commercial AA methanol. This purified oxygenate containing stream is used in one embodiment as the oxygenate feed stream. Non-limiting examples of a process for producing an oxygenate feed stream from hydrocarbons and using it to produce olefins is described in EP-B-0 933 345, which is herein fully incorporated by reference.

The feed stream, preferably an oxygenate feed stream, in one embodiment, contains one or more diluents, typically used to reduce the concentration of the active ingredients in the feed stream, and are generally non-reactive to the active ingredients in the feed stream or molecular sieve catalyst composition. Non-limiting examples of diluents are disclosed in PCT Publication Nos. WO 03/000412 and WO 03/000413, the contents of which are incorporated herein by reference. The most preferred diluents are water and nitrogen, with water being particularly preferred.

In one embodiment, other hydrocarbons are added to the feed stream, preferably oxygenate feed stream, either directly or indirectly, and include olefin(s), paraffin(s), aromatic(s) (see for example, U.S. Pat. No. 4,677,242, addition of aromatics) or mixtures thereof, preferably propylene, butene, pentene, and other hydrocarbons having 4 or more carbon atoms, or mixtures thereof.

As noted, oxygenate-to-olefin processes typically use molecular sieve catalysts or molecular sieve catalyst compositions. The molecular sieve catalyst compositions have molecular sieve and binder and/or matrix material. The molecular sieve catalysts are prepared according to techniques that are known to a person of ordinary skill in the art.

Molecular sieves are disclosed in PCT Publication Nos. WO 03/000412 and WO 03/000413, the contents of which are incorporated herein by reference. Preferably, the molecular sieve is a zeolitic or zeolitic-type molecular sieve. Alternatively, the preferred molecular sieve is an aluminophosphate (ALPO) molecular sieves and/or silicoaluminophosphate (SAPO) molecular sieves and substituted, preferably metal substituted, ALPO and/or SAPO molecular sieves including the molecular sieves that are intergrowth materials having two or more distinct phases of crystalline structures within one molecular sieve composition.

Binder materials that are useful alone or in combination include various types of hydrated alumina, silicas, and/or other inorganic oxide sol. In one embodiment, the binders are alumina sols including Nalco 8676 available from Nalco Chemical Co., Naperville, Ill. and Nyacol available from The PQ Corporation, Valley Forge, Pa.

Matrix materials include one or more of: rare earth metals, metal oxides including titania, zirconia, magnesia, thoria, beryllia, quartz, silica or sols, and mixtures thereof, for example, silica-magnesia, silica-zirconia, silica-titania, silica-alumina and silica-alumina-thoria. In an embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite.

The process for converting a feed stream, especially an oxygenate feed stream in the presence of a molecular sieve catalyst composition is carried out in a reaction process in a reactor, where the process is a fixed bed process, a fluidized bed process, preferably a continuous fluidized bed process, and most preferably a continuous high velocity fluidized bed process.

The reaction processes can take place in a variety of catalytic reactors such as hybrid reactors that have a dense bed or fixed bed zones and/or fast fluidized bed reaction zones coupled together, circulating fluidized bed reactors, riser reactors, and the like. Suitable conventional reactor types are described in, for example, U.S. Pat. No. 4,076,796, U.S. Pat. No. 6,287,522 (dual riser), and Fluidization Engineering, D.

Kunii and O. Levenspiel, Robert E. Krieger Publishing Company, New York, N.Y. 1977, which are all herein fully incorporated by reference.

The preferred oxygenate-to-olefin reactor is a riser reactor. Riser reactors are generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

The various feed streams, preferably oxygenate feed streams, discussed above are converted primarily into one or more olefin(s). The olefin(s) or olefin monomer(s) produced from the feed stream typically have from 2 to 30 carbon atoms, preferably 2 to 8 carbon atoms, more preferably 2 to 6 carbon atoms, still more preferably 2 to 4 carbons atoms, and most preferably ethylene and/or propylene.

Non-limiting examples of olefin monomer(s) include ethylene, propylene, butene-1, pentene-1, 4-methyl-pentene-1, hexene-1, octene-1 and decene-1, preferably ethylene, propylene, butene-1, pentene-1, 4-methyl-pentene-1, hexene-1, octene-1 and isomers thereof. Other olefin monomer(s) include unsaturated monomers, diolefins having 4 to 18 carbon atoms, conjugated or non-conjugated dienes, polyenes, vinyl monomers and cyclic olefins. See PCT Publication Nos. WO 03/000412 and WO 03/000413 for a more complete description of the olefins produced. The contents of these publications are incorporated herein by reference. Most preferably, the olefin(s) produced are ethylene, propylene or butene often referred to as prime olefin(s) or light olefins.

In one embodiment, the reactor effluent stream comprises about 5 wt. % or less, preferably about 1.0 wt. % or less, more preferably about 0.5 wt. % or less, typically about 0.001 wt. % catalyst fines.

In one embodiment, the reactor effluent stream comprises ethylene and propylene, C4+ olefins, methane, C2+ paraffins, aromatic compounds, water, unreacted oxygenate feed stream, and oxygenate hydrocarbons as the reactor effluent stream leaves the reactor. In another embodiment, the reactor effluent stream comprises from about 30 wt. % to about 70 wt. % water, preferably, from about 35 wt. % to about 70 wt. % water; more preferably from about 40 wt. % to about 65 wt. % water expressed as a percentage of the total weight of the reactor effluent stream. In one embodiment of the process for conversion of an oxygenate feed stream, the amount of olefin(s) produced is greater than 50 weight percent, preferably greater than 60 weight percent, more preferably greater than 70 weight percent, and most preferably greater than 75 weight percent based upon total weight of hydrocarbons in the effluent stream as the effluent stream leaves the reactor.

There is an embodiment according to any process disclosed herein wherein the effluent stream comprises from about 0.05 wt. % to about 5 wt. %, preferably from about 0.1 wt. % to about 3 wt. %, more preferably from about 0.2 wt. % to about 3 wt. %, even more preferably from about 1 wt. % to about 2 wt. %, most preferably of about 1.5 wt. % alcohol (typically methanol) based upon the composition of the effluent stream as the effluent stream leaves the reactor.

There is an embodiment according to any process disclosed herein wherein the effluent stream comprises from about 0.01 wt. % to about 5 wt. %, preferably from about 0.01 wt. % to about 3 wt. %, more preferably from about 0.05 wt. % to about 2 wt. %, even more preferably from about 0.05 wt. % to about 1 wt. %, most preferably of about 0.05 wt. % organic acids based upon the composition of the effluent stream as the effluent stream leaves the reactor. By organic acids it is meant acids that are made of organic material, i.e. hydrogen atoms bound to carbon atoms. For the purpose of this application, organic acids include organic acids in their corresponding salt form. For example, organic acids will include formic acid as well as formate salts, acetic acid as well as acetate salts, propanoic acid as well as propanoate salts, butyric acids as well as butyrate salts.

There is an embodiment according to any process disclosed herein wherein the effluent stream comprises about 5 wt. % or less, preferably about 3 wt. % or less, more preferably about 1 wt. % or less aromatic compounds based upon the composition of the effluent stream as the effluent stream leaves the reactor.

There is an embodiment according to any process disclosed herein wherein the effluent stream comprises about 0.3 wt. % or less, preferably about 0.1 wt. % or less, more preferably about 0.05 wt. % or less, most preferably less than detectable levels of nitrogen containing compounds based upon the composition of the effluent stream as the effluent stream leaves the reactor. In one embodiment, the effluent stream comprises about 10 wppm or less, preferably about 5 wppm or less, more preferably about 1 wppm or less, most preferably less than detectable levels of nitrogen containing compounds based upon the composition of the effluent stream as the effluent stream leaves the reactor.

There is an embodiment according to any process disclosed herein wherein the effluent stream comprises about 0.3 wt. % or less, preferably about 0.1 wt. % or less, more preferably about 0.01 wt. % or less, most preferably less than detectable levels of sulfur containing compounds based upon the composition of the effluent stream as the effluent stream leaves the reactor. In one embodiment, the effluent stream comprises about 10 wppm or less, preferably about 5 wppm or less, more preferably about 1 wppm or less, most preferably less than detectable levels of sulfur containing compounds based upon the composition of the effluent stream as the effluent stream leaves the reactor.

There is one embodiment according to any of the processes disclosed herein, wherein the effluent stream comprises about 0.3 wt. % or less; preferably about 0.05 wt. % or less; more preferably about 0.01 wt. % or less, most preferably less than detectable levels of halogen (typically chlorine) containing compounds based upon the composition of the effluent stream. In one embodiment, the effluent stream comprises about 10 wppm or less, preferably about 5 wppm or less, more preferably about 1 wppm or less, most preferably less than detectable levels of halogen containing compounds based upon the composition of the effluent stream as the effluent stream leaves the reactor.

The reactor effluent stream is transported along line 24 to a quench device 30. According to one embodiment, the reactor effluent stream has a dewpoint. Dewpoint is the temperature that a gaseous stream first condenses. The reactor effluent stream remains at a temperature above the dewpoint while it is transported from the reactor effluent stream to the quench device 30.

In one embodiment illustrated in FIG. 2, the outlet of reactor effluent stream is in fluid communication with a heat exchanger system 26 on line 24 to cool the effluent stream. According to one embodiment, the heat exchanger system 26 comprises one or more heat exchanger services, preferably two to four heat exchanger services, most preferably two or three heat exchanger services.

Quench, Compression, and Catalyst Fines Separation from Quench Bottoms

The oxygenate-to-olefin process forms a substantial amount of water as a byproduct. Furthermore, a substantial amount of catalyst fines are carried in the effluent stream. The outlet of the reactor, in one embodiment, is in fluid communication with the quench device 30 by a conduit represented by line 24. Among other things, water and catalyst fines can be removed from the reactor effluent stream by a quench device 30. A "quench device" is a device for removing a portion of the reactor effluent stream by establishing a sufficient quantity of a liquid phase in contact with the reactor effluent stream which condenses at least a portion of the material in the reactor effluent stream. One example of a quench device in an oxygenate-to-olefin product stream is found in U.S. Pat. No. 6,121,504 (direct product quench). The liquid matter that contacts the reactor effluent stream and causes the condensation is called a "quench medium."

In a quench device 30, at least a portion of the reactor effluent stream is rapidly condensed through contact with a quench medium in the liquid state. When quenching in a quench device 30, at least a portion of the reactor effluent stream remains in a gaseous state and another portion is condensed to form a liquid.

The portion of the effluent stream that remains in a gaseous state after at least one step of quenching is the quenched effluent stream. The quenched effluent stream is withdrawn through the overhead of the quench device—in one embodiment along line 33. The portion of the reactor effluent stream that is gaseous under quenching conditions typically comprises light olefins, dimethyl ether, methane, carbon monoxide, carbon dioxide, ethane, propane, and any water and unreacted oxygenate feed stream that is not condensed during the operation of the quench device 30.

The portion of the reactor effluent stream that is condensed under quench conditions is the liquid fraction. The liquid fraction of one embodiment is withdrawn through the bottoms of the quench device as a quench bottoms stream. In one embodiment, the quench bottoms stream is withdrawn in one or more streams. According to the embodiment of FIG. 2, the quench bottoms stream is withdrawn along line 34. The liquid fraction of one embodiment comprises water; dissolved carbon dioxide; organic acids such as formic acid, acetic acid, propanoic acid and butyric acid (either dissolved or in a salt form); aromatic compounds; a portion of the unreacted oxygenate feed stream (typically alcohols, e.g. methanol); and other heavy hydrocarbons (e.g. C5+ hydrocarbons). Furthermore, the liquid fraction tends to capture a majority of the catalyst fines that are carried in the reactor effluent stream.

According to one embodiment of the present invention, a quench tower is employed as a quench device. In a quench tower, the reactor effluent stream is intimately contacted (i.e., directly exposed in a common volume, and not separated by walls as described above for a heat exchanger) with a quench medium in the liquid state. The quench medium is introduced to the quench tower at a temperature that is both below the quench medium bubble point temperature and the effluent stream dew point temperature. The quench medium is introduced in sufficient volume to cause the reactor effluent stream to move rapidly below its dew point temperature such that a substantial portion of the reactor effluent stream rapidly condenses.

The quench medium, according to one method of use, is introduced into the quench device at a location or locations above where the reactor effluent stream is introduced, such that the quench medium will fall within the quench tower and be contacted with the reactor effluent stream as it, or portions of it including the olefins in a gaseous state, rise through the tower.

The quench tower typically includes internal elements to facilitate intimate contacting of the quench medium with the reactor effluent stream or portions thereof, including liquid distributors and contacting devices such as baffles, trays or structured packing. Intimate contacting with a liquid quench medium facilitates drawing catalyst fines out of the reactor effluent stream, into a free-flowing, dilute liquid phase and away from at least a portion of the olefins in a gaseous state. The quench tower usually also include other elements, such as heat exchangers used to cool the quench medium that is recirculated into the quench tower.

In a particular embodiment, the quench medium is water. In another embodiment, the quench medium is a portion of the quench bottoms stream that has been recovered from the bottoms stream of the quench device 30 along line 34. It is redirected along line 36, cooled in a heat exchanger 38 and reintroduced into the quench device along line 36.

In one embodiment, some or all of the quench medium is supplied along line 32 to the quench device 30. Additional quench medium, includes, water that is free of catalyst fines and/or other components of the quench bottoms stream. In one embodiment, the pH is adjusted by adding a neutralizing agent and/or an alkaline agent to the quench bottoms stream and/or quench medium. The pH of the quench medium ranges from about 6 to about 8, preferably from about 6.5 to about 7.5, more preferably about 7. In another embodiment, the quench medium is adjusted to have a pH of 7 or higher; preferably about 7.1 or higher; more preferably from 7.5 to about 11; even more preferably from about 8.5 to about 10.5; most preferably about 9.

According to one embodiment, the quench bottoms stream has about 5 wt. % or less, typically about 1 wt. % or less, often from about 0.5 wt. % or less catalyst fines based upon the composition of the quench bottoms stream.

There is an embodiment according to any process disclosed herein wherein the quench bottoms stream further comprises about 5 wt. % or less, preferably about 4 wt. % or less, more preferably from about 3.5 wt. % or less alcohol (typically methanol) based upon the composition of the quench bottoms stream as the quench bottoms stream leaves the quench device.

There is an embodiment according to any process disclosed herein wherein the quench bottoms stream further comprises from about 0.001 wt. % to about 5 wt. %, preferably from about 0.002 wt. % to about 3 wt. %, more preferably from about 0.005 wt. % to about 2 wt. %, even more preferably from about 0.005 wt. % to about 1.0 wt. %, most preferably of about 0.01 wt. % organic acids based upon the composition of the quench bottoms stream as the quench bottoms stream leaves the quench device.

There is an embodiment according to any process disclosed herein wherein the quench bottoms stream further comprises about 5 wt. % or less, preferably about 3 wt. % or less, more preferably about 1 wt. % or less aromatic compounds based upon the composition of the quench bottoms stream as the quench bottoms stream leaves the quench device.

There is an embodiment according to any process disclosed herein wherein the quench bottoms stream comprises about 0.1 wt. % or less, preferably about 0.5 wt. % or less, more preferably about 0.01 wt. % or less, even more preferably about 0.005 wt. % or less, most preferably less than detectable levels of nitrogen containing compounds, based upon the composition of the quench bottoms stream as it leaves the quench device. In one embodiment, the quench bottoms stream comprises about 10 wppm or less, preferably about 5 wppm or less, more preferably about 1 wppm or less, most preferably less than detectable levels of nitrogen containing compounds based upon the composition of the quench bottoms stream as the quench bottoms stream leaves the quench device.

There is an embodiment according to any process disclosed herein wherein the quench bottoms stream comprises about 0.1 wt. % or less, preferably about 0.05 wt. % or less, more preferably about 0.01 wt. % or less, most preferably less than detectable levels of sulfur containing compounds, based upon the composition of the quench bottoms stream as it leaves the quench device. In one embodiment, the quench bottoms stream comprises about 10 wppm or less, preferably about 5 wppm or less, more preferably about 1 wppm or less, most preferably less than detectable levels of sulfur containing compounds based upon the composition of the quench bottoms stream as the quench bottoms stream leaves the quench device.

There is an embodiment according to any process disclosed herein wherein the quench bottoms stream comprises about 0.1 wt. % or less, preferably about 0.05 wt. % or less, more preferably about 0.01 wt. % or less, most preferably less than detectable levels of halogen (typically chlorine) containing compounds, based upon the composition of the quench bottoms stream as it leaves the quench device. In one embodiment, the quench bottoms stream comprises about 10 wppm or less, preferably about 5 wppm or less, more preferably about 1 wppm or less, most preferably less than detectable levels of halogen (typically chlorine) containing compounds based upon the composition of the quench bottoms stream as the quench bottoms stream leaves the quench device.

There is an embodiment according to any process disclosed herein wherein the quench bottoms stream comprises about 1 wt. % or less, preferably about 0.5 wt. % or less, more preferably about 0.1 wt. % or less, most preferably less than detectable levels of metal ion salts, based upon the composition of the quench bottoms stream as it leaves the quench device. Additionally, the quench bottoms stream comprises red oil, if any, from the aldol condensation of aldehydes and ketones.

The quench bottoms stream, of one embodiment, is separated in a liquid/liquid separation zone where a phase separation occurs between a hydrocarbon phase and an aqueous phase. In one embodiment, the liquid/liquid separation zone is located at the bottoms of the quench device. Particularly, there is a weir formed in the bottom of the quench device that separates the aqueous phase from the hydrocarbon phase.

In another embodiment disclosed in FIG. 2, the quench bottoms stream is transported along line 34 to a liquid/liquid separation vessel 35 such as a tank or drum. The liquid/liquid separation vessel 35 separates the hydrocarbon phase and withdraws it along line 37. The aqueous phase is withdrawn along line 39.

The hydrocarbon phase optionally comprises red oil (produced from the aldol condensation of aldehydes and ketones) and any aromatic compounds including alkylated aromatics. The aqueous phase comprises water, catalyst fines, organic acids in the salt form, metal salts, unreacted oxygenate feed stream including alcohols (eg. methanol).

The hydrocarbon phase is transported along line 37 and is processed according to techniques known in the relevant technology. The aqueous phase of the liquid fraction is transported from the separation tank 35 along line 39. Optionally, water from other locations in the oxygenate to olefin process is added to the separation tank 35 (or alternatively the aqueous phase of the quench bottoms stream in line 42). Such locations include, by way of example and not by limitation, knock-out drums in the compression train, used oxygenate wash medium, used water wash medium following the caustic wash, other water washes.

The quench bottoms stream, or the aqueous phase of the quench bottoms stream, undergoes a heavy fraction removal step. By heavy fraction it is meant a fraction comprising components having a relative volatility less than or equal to water including solid components without any relative volatility. In one embodiment the heavy fraction removal step is processed in a first separation stage. The first separation stage separates the aqueous phase of the quench bottoms into a first vapor fraction and a first residual fraction. The first vapor fraction, of one embodiment, comprises water and unreacted oxygenate feed such as alcohol and/or dimethyl ether. Additionally, any aldehydes, ketones or other oxygenates are present in the first vapor fraction of one embodiment. The first residual fraction, or heavy fraction, of one embodiment comprises water, organic acids in their salt form (i.e. formate, acetate, propanoate, butyrate) inorganic salts including disolved salt forms of carbon dioxide, metal salts, catalyst fines and other particulates. According to one embodiment, the first separation stage uses a distillation tower, a stripping tower, or any vaporization system.

In one embodiment the first separation stage is illustrated in FIG. 2. The quenched effluent stream passes through a heat exchanger 44. The heat exchanger 44 partially boils the quench bottoms stream that is in line 39. The partially boiled effluent stream passes through a separation vessel 46 The quench bottoms stream forms a residual fraction as described above. The residual fraction is withdrawn from separation vessel 46 along line 50 and is treated as described below. The first vapor fraction is withdrawn from the separation vessel along line 48 where it is treated with a light fraction removal step.

According to one embodiment, the quench bottoms stream, or the aqueous phase of the quench bottoms stream, undergoes a light fraction removal step. In one embodiment, the light fraction removal step follows the heavy fraction removal step. In another embodiment, the light fraction removal step precedes the heavy fraction removal step. By "light hydrocarbon fraction" it is meant hydrocarbons, including oxygenate hydrocarbons, that have a relative volatility that is greater than or equal to water. In one embodiment, the light hydrocarbon fraction includes but are not limited to alcohol feed (eg. methanol and ethanol) as well as aldehydes, ketones or other oxygenates, if any. The separation of the light hydrocarbon fraction is made by any technique known in the art, including distillation, extractive distillation, liquid/liquid extraction, or stripping tower. The water from the quench bottoms stream is purified to process quality water after separation to remove a heavy residual fraction and light hydrocarbon fraction as discussed above. By process quality water it is meant water that is in an acceptable condition for use as boiler feed water makeup and or cooling tower water make-up. In one embodiment, process water is used as feed to a syngas reformer that in turn produces syngas for methanol production.

According to one embodiment, the process quality water has about 0.5 wt. % or less, preferably about 0.1 wt. % or less; more preferably about 0.01 wt. % catalyst fines based upon the composition of the process quality water.

There is an embodiment according to any process disclosed herein wherein the process quality water comprises about 0.1 wt. % or less, preferably about 0.03 wt. % or less, more preferably about 100 wppm or less, most preferably about 10 wppm or less alcohol based upon the composition of the process quality water.

There is another embodiment according to any process disclosed herein wherein the process quality water further comprises less than about 0.1 wt. %, preferably less than about 0.03 wt. %, more preferably less than 100 wppm, even more preferably less than 10 wppm methanol based upon the composition of the process quality water.

There is an embodiment according to any process disclosed herein wherein the process quality water comprises less than about 0.1 wt. %, preferably less than about 0.03 wt. %, more preferably less than 100 wppm, even more preferably less than 10 wppm organic acids based upon the composition of the process quality water.

There is an embodiment according to any process disclosed herein wherein the process quality water comprises about 0.01 wt. % or less, preferably about 10 wppm or less, most preferably about 5 wppm or less aromatic compounds based upon the composition of the process quality water.

The byproduct water is used in one embodiment of the present invention to satisfy the water requirement. In one embodiment, at least 25 wt. %, typically 30 wt. %, preferably 40 wt. % or more, more preferably 50 wt. % or more, most preferably about 60 wt. % or more, typically from about 70 wt. % to about 90 wt. % or more of the byproduct water is reused in the process for the water requirement of the process. By water requirement, it is meant, the amount of water consumed in an oxygenate to olefin process by steps or applications that consume water without recovering the water in the process. For example, water is used as boiler feed water makeup or cooling tower makeup. In each of these applications, a portion of the water is openly evaporated or withdrawn through a blowdown and/or leaves the process without recovery. In contrast, water used in a quench leaves the quench as a vapor with water saturated quenched effluent stream or is removed through the bottoms stream of the quenched effluent stream. In either case, the water is recovered through the water recovery process described herein, thus there is no net loss of water. Likewise, use of water in water wash system or caustic wash systems typically do not have a water requirement.

In another embodiment, at least 30 wt. %, preferably 40 wt. % or more, more preferably from about 40 wt. % to about 90 wt. %, even more preferably from about 40 wt. % to about 80 wt. %, most preferably from about 40 wt. % to about 70 wt. % of the water requirement of process are satisfied by byproduct water. Such water requirement includes any use in the plant that results in a net consumption of water.

According to one embodiment illustrated in FIG. 2, the quench bottoms stream leaves the separation vessel 46 along line 48 after the residual fraction is removed. The quench bottoms stream is carried along line 48 to a cooler/condenser 52 where water in the quench bottoms stream is at least partially condensed. The partial condensation liquifies a portion of the water. This condensation causes a phase separation between the liquified quench bottoms stream comprising water 58 and the gaseous quench bottoms stream comprising water and light hydrocarbon fraction in a separation vessel 54. The liquified quench bottoms comprising water is typically useful for quench water or water as an absorbent in a liquid/liquid extractor if any. In one embodiment, the liquified quench bottoms comprising water is useful as process quality water.

The portion of the quench bottoms stream that remains in vapor form is withdrawn from the separation vessel 54 along line 56 to a distillation tower 62. Additional oxygenates from an oxygenate wash, i.e. an alcohol wash, preferably a methanol wash, are optionally added to the quench bottoms stream via line 60.

The distillation tower 62 separates the light hydrocarbon fraction from water.

By separate, it is meant that at least a majority of the water is condensed into a distillation tower bottoms stream such that the distillation tower bottoms stream produces a process quality water and is withdrawn along line 68. The light hydrocarbon fraction is withdrawn in vapor form from the distillation tower 62 through an overhead stream represented by line 64. The light hydrocarbon fraction is recycled to the oxygenate to olefin reactor 22, in one embodiment. In another embodiment, the light hydrocarbon fraction is further fractionated into one or more of its components and used for a purpose known for such component by those of ordinary skill in the art.

The treatment of the residual fraction is now described below with reference to FIG. 2, the residual fraction is withdrawn along line 50 to a settling tank 70. A settling tank is a separation device. A separation device is any device that separates solids from liquid by the relative density of the solid and liquid. Examples of separation devices include settling devices and centrifugal separators such as a centrifuge. One separation device is a settling device. A settling device is defined as a device that separates solid particulate from liquid using gravitational force. According to one embodiment, the settling device is selected from the group consisting of clairifiers, settling tanks, and settling ponds.

The solid particles are separated from the first liquid stream by settling the solid particles to the bottom of the settling tank 70 forming concentrated solid particles and an at least partially clarified residual fraction. The at least partially clarified residual fraction results from the sedimentation of the solid particles in the settling tank 70. The concentrated catalyst fines are withdrawn along line 72 or are alternatively removed by any means known in the art.

To aid in the efficient removal of catalyst fines from the first liquid stream, a flocculent is added along line 71 in one embodiment. Flocculent is defined as material added to a liquid and solids mixture, which enhances the density differences between the solid and liquid and hence improves the sedimentation process. The flocculent enhances the settling of the solid particles to the bottom of the settling tank 70. According to one embodiment, the time it takes for effective separation with the flocculent is about 2.5 hours or less, preferably about 2.0 hours or less, more preferably about 1.5 hours or less, most preferably about 1.0 hours or less. Effective separation as used herein pertains to separation of a liquid portion from a solid portion in a liquid/solid mixture. Effective separation occurs when the at least partially clarified residual fraction contains about 1 wt. % or less of the solids that were present in the solid/liquid mixture.

In one embodiment the flocculent is a cationic polymer. Preferably, the flocculent is a cationic polymer selected from the group consisting of: polyacryamides, diallyldimethyl amonium chloride, epichlorohydrin-amine, and dicandiamide-formaldehyde.

According to one embodiment, the ratio of the weight of the catalyst fines to the weight of the flocculent is less than the amount at which the given flocculent results in overdosing. Overdosing occurs when more flocculent is added than is needed to settle the solid particles. Overdosing is often measured by the presence of flocculent in the activated sludge or water stream.

The partially clarified residual fraction is withdrawn from the settling device along line 74. In one embodiment, the partially clarified liquid fraction is conveyed to settling pond 76. Any remaining solid particles can be settled out in the settling pond 76. The use of a flocculent is optional to aid in the settling of solid particles. Optionally, the flocculent is added along line 78. Furthermore, living organism reside in the settling pond 76 that consume the organic acids, typically in their salt form, and any other organic components that is present in the water, for example methanol and ethanol. After the settling pond 76, the water is further processed for safe release into the environment along line 80.

As previously described the reactor effluent stream is quenched to remove catalyst fines and water in the reactor effluent stream and produces a quenched effluent stream. The quenched effluent stream is further processed by compressing the stream. Then, as described below, the quenched effluent stream is washed to remove acid gasses and alternatively other oxygenates. Following the washing, the quenched effluent stream is dried to remove water in accordance with the description below.

Product Washing and Drying

According to one embodiment, the quenched effluent stream is transported to an optional oxygenate wash tower which removes oxygenates by extraction with an oxygenate wash medium. An oxygenate wash medium is any medium that effectively adsorbs oxygenates but does not adsorb olefins, relatively. The oxygenate wash tower introduces a wash medium, preferably at the top of the wash tower. The oxygenates are removed through an oxygenate wash tower bottoms stream. It is optionally transported and combined with the quench bottoms stream for processing oxygenate and light hydrocarbon removal.

All or part of the oxygenates such as ethers, aldehydes and/or ketones that are remaining in the quenched effluent stream are optionally removed during the oxygenate wash step. In one preferred embodiment, dimethyl ether, acetaldehyde, propanal and propanone are optionally removed in the oxygenate wash tower.

In one embodiment of the invention, oxygenate wash medium is added to the oxygenate wash tower in an amount sufficient to substantially reduce oxygenate content. It is preferred that oxygenate wash medium is added to the vessel at a molar ratio of oxygenate wash medium to quenched effluent stream from about 4:1 to about 1:5,000 based upon the composition of the quenched effluent stream.

Higher molar ratios of oxygenate wash medium to quenched effluent stream are desirable for reducing oxygenate content; preferably from about 4:1 to about 1:1, more preferably from about 3:1 to about 1.2:1, and most preferably from about 2.5:1 to about 1.5:1.

Examples of oxygenate wash mediums include alcohols, amines, amides, nitrites, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

The quenched effluent stream that, optionally, passes through the oxygenate wash tower is typically treated with an alkaline wash.

An alkaline wash or adsorbent is used to remove carbon dioxide from the quenched effluent stream in the first fraction by contacting the first fraction with an alkaline wash medium according to one embodiment. The alkaline wash medium is a medium that has a pH greater than 7. Examples of such alkaline wash mediums include amines, potassium carbonate, caustic and alumina. Examples of some carbon dioxide absorbents include molecular sieves and membranes, particularly membranes formed of polysulfone, polyimid, polyamide, glassy polymer and cellulose acetate. Solutions containing amines and caustic compounds are preferred, with caustic compounds being more preferred.

The alkaline wash medium removes any remaining carbon dioxide from the quenched effluent stream. In an embodiment, the alkaline wash stage washes the effluent with an alkaline stream having a pH greater than about 13.

According to one embodiment, the circulated alkaline stream has an alkaline concentration of 1 wt. % or more, preferably from about 1 wt. % to about 5 wt. %, more preferably from about 2 wt. % to about 5 wt. %, most preferably of about 3 wt. % based upon the composition of the alkaline stream. Any one or more of the alkaline compounds listed or represented above are added to the alkaline wash at higher concentrations than is circulated. Fresh caustic makeup typically has a concentration ranging from about 15 wt. % to about 50 wt. % sodium hydroxide based upon the total concentration of the caustic makeup.

The washed effluent stream leaving the alkaline wash and water wash, of one embodiment, has a concentration of carbon dioxide of less than about 1000 ppb, preferably less than about 300 ppb, more preferably less than 50 ppb carbon dioxide based upon composition of the washed effluent stream.

The quenched effluent stream passes through an additional stage of washing referred to as the water wash stage. Water is contacted with the quenched effluent stream. The water wash removes any remaining alkaline wash medium in the quenched effluent stream or olefin stream. The washing step produces a washed effluent stream that is thereafter typically dried prior to fractionation into specific product streams.

A drying step is optionally included. In this embodiment, a solid or liquid drying system can be used to remove water and/or additional oxygenated hydrocarbon from the quenched effluent stream.

In the solid drying system, the quenched effluent stream having been optionally alkaline washed and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that may not normally be removed by using other treatment systems. Preferably, an adsorbent system used as part of this invention has multiple adsorbent beds. Multiple beds allow for continuous separation without the need for shutting down the process to regenerate the solid adsorbent. By way of example and not by limitation, a three bed system typically has one bed that is on-line, one bed regenerated off-line, and a third bed on stand-by.

The specific adsorbent solid or solids used in the adsorbent beds depends on the types of contaminants being removed. Non-limiting examples of solid adsorbents for removing water and various polar organic compounds, such as oxygenated hydrocarbons and absorbent liquids, include aluminas, silica, 3A molecular sieves, 4A molecular sieves, and alumino-silicates. Beds containing mixtures of these sieves or multiple beds having different adsorbent solids are used to remove water, as well as a variety of oxygenated hydrocarbons in one embodiment.

In an embodiment of this invention, one or more adsorption beds are arranged in series or parallel. In one example of a series arrangement, a first bed is used to remove the smallest and most polar molecules, which are the easiest to remove. Subsequent beds for removing larger less polar oxygenated species are next in series. As a specific example of one type of arrangement, water is first selectively removed using a 3A molecular sieve. This bed is then followed by one or more beds containing one or more less selective adsorbents such as a larger pore molecular sieve e.g. 13X and/or a high surface area active alumina such as Selexorb CD (Alcoa tradename).

In another embodiment, the first bed is a 3.6A molecular sieve capable of selectively removing both water and methanol. This bed can then be followed by one or more 13X or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the quenched effluent stream. The water absorbent can be any liquid effective in removing water from an olefin stream. Preferably, the water absorbent is a polyol or an alcohol, such as ethanol or methanol.

Preferably the olefin stream after the step of washing and drying has a water content that is less than about 100 wppm water, more preferably less than about 10 wppm, and most preferably less than 1 wppm. The step of acid washing and drying produces a dried olefin stream that is substantially free of water and carbon dioxide.

Product Recovery

The dried olefin stream, or olefin product stream, is further processed to isolate and purify components in the effluent stream, particularly, ethylene and propylene. There are many well-known recovery systems, techniques and sequences that are useful in separating olefin(s) and purifying olefin(s) in the dried effluent stream. Recovery systems generally comprise one or more or a combination of a various separation, fractionation and/or distillation towers, columns, splitters, or trains, reaction systems and other associated equipment, for example, various condensers, heat exchangers, refrigeration systems or chill trains, compressors, knock-out drums or pots, pumps, and the like.

Non-limiting examples of equipment used in a recovery system include one or more of a demethanizer, preferably a high temperature demethanizer, a dethanizer, a depropanizer, membranes, ethylene (C2) splitter, propylene (C3) splitter, butene (C4) splitter, and the like.

Various recovery systems useful for recovering predominately olefin(s), preferably prime or light olefin(s) such as ethylene, propylene and/or butene are described in U.S. Pat. No. 5,960,643 (secondary rich ethylene stream), U.S. Pat. Nos. 5,019,143, 5,452,581 and 5,082,481 (membrane separations), U.S. Pat. No. 5,672,197 (pressure dependent adsorbents), U.S. Pat. No. 6,069,288 (hydrogen removal), U.S. Pat. No. 5,904,880 (recovered methanol to hydrogen and carbon dioxide in one step), U.S. Pat. No. 5,927,063 (recovered methanol to gas turbine power plant), and U.S. Pat. No. 6,121,504 (direct product quench), U.S. Pat. No. 6,121,503 (high purity olefins without superfractionation), and U.S. Pat. No. 6,293,998 (pressure swing adsorption), which are all herein fully incorporated by reference.

Generally accompanying most recovery systems is the production, generation or accumulation of additional products, by-products and/or contaminants along with the preferred prime products. The preferred prime products, the light olefins, such as ethylene and propylene, are typically purified for use in derivative manufacturing processes such as polymerization processes. Therefore, in the most preferred embodiment of the recovery system, the recovery system also includes a purification system. For example, the light olefin(s) produced particularly in an oxygenate-to-olefin process are passed through a purification system that removes low levels of by-products or contaminants.

Non-limiting examples of contaminants and by-products include generally polar compounds such as water, alcohols, carboxylic acids, ethers, carbon oxides, ammonia and other nitrogen compounds, arsine, phosphine and chlorides. Other contaminants or by-products include hydrogen and hydrocarbons such as acetylene, methyl acetylene, propadiene, butadiene and butyne.

Other recovery systems that include purification systems, for example, for the purification of olefin(s), are described in Kirk-Othmer Encyclopedia of Chemical Technology, 4th Edition, Volume 9, John Wiley & Sons, 1996, pages 249-271 and 894-899, which is herein incorporated by reference. Purification systems are also described in, for example, U.S. Pat. No. 6,271,428 (purification of a diolefin hydrocarbon stream), U.S. Pat. No. 6,293,999 (separating propylene from propane), and U.S. patent application Ser. No. 09/689,363 filed Oct. 20, 2000 (purge stream using hydrating catalyst), which is herein incorporated by reference.

Typically, in converting one or more oxygenates to olefin(s) having 2 or 3 carbon atoms, an amount of hydrocarbons, particularly olefin(s), especially olefin(s) having 4 or more carbon atoms, and other by-products are formed or produced. Included in the recovery systems of the invention are reaction systems for converting the products contained within the effluent stream withdrawn from the reactor or converting those products produced as a result of the recovery system utilized.

In one embodiment, the olefin product stream is passed through a recovery system producing one or more hydrocarbon containing stream(s), in particular, a three or more carbon atom (C3+) hydrocarbon containing stream. In this embodiment, the C3+ hydrocarbon containing stream is passed through a first fractionation zone producing a crude C3 hydrocarbon and a C4+ hydrocarbon containing stream, the C4+ hydrocarbon containing stream is passed through a second fractionation zone producing a crude C4 hydrocarbon and a C5+ hydrocarbon containing stream. The four or more carbon hydrocarbons include butenes such as butene-1 and butene-2, butadienes, saturated butanes, and isobutanes.

The effluent stream removed from a conversion process, particularly an oxygenate-to-olefin process, typically has a minor amount of hydrocarbons having 4 or more carbon atoms. The amount of hydrocarbons having 4 or more carbon atoms is typically in an amount less than 30 weight percent, preferably less than 25 weight percent, more preferably less than 20 weight percent, and most preferably less than 15 weight percent, based on the composition of the effluent stream withdrawn from an oxygenate-to-olefin process, excluding water. In particular with a conversion process of oxygenates into olefin(s) utilizing a molecular sieve catalyst composition the resulting effluent stream typically comprises a majority of ethylene and/or propylene and a minor amount of four carbon and higher carbon number products and other by-products, excluding water.

The preferred light olefin(s) produced by any one of the processes described above, preferably conversion processes, are high purity prime olefin(s) products that contains a CX olefin, wherein x is a number from 2 to 4, in an amount greater than 80 wt. %, preferably greater than 90 wt. %, more preferably greater than 95 wt. %, and most preferably no less than about 99 wt. %, based on the composition of the olefin. The purity of the olefins is preferably of a grade that makes the use of the olefins acceptable for one or more applications discussed below.

Olefin Product Use

Suitable well-known reaction systems that follow the recovery system primarily take lower value products and convert them to higher value products. For example, the C4 hydrocarbons, butene-1 and butene-2 are used to make alcohols having 8 to 13 carbon atoms, and other specialty chemicals, isobutylene is used to make a gasoline additive, methyl-t-butylether, butadiene in a selective hydrogenation unit is converted into butene-1 and butene-2, and butane is useful as a fuel.

Non-limiting examples of reaction systems that take lower value products and convert them to higher value products include U.S. Pat. No. 5,955,640 (converting a four carbon product into butene-1), U.S. Pat. No. 4,774,375 (isobutane and butene-2 alkylated to an alkylate gasoline), U.S. Pat. No. 6,049,017 (dimerization of n-butylene), U.S. Pat. Nos. 4,287, 369 and 5,763,678 (carbonylation or hydroformulation of higher olefins with carbon dioxide and hydrogen making carbonyl compounds), U.S. Pat. No. 4,542,252 (multistage adiabatic process), U.S. Pat. No. 5,634,354 (olefin-hydrogen recovery), and Cosyns, J. et al., Process for Upgrading C3, C4 and C5 Olefinic Streams, Pet. & Coal, Vol. 37, No. 4 (1995) (dimerizing or oligomerizing propylene, butylene and pentylene), which are all herein fully incorporated by reference.

Other uses for one or more olefin products are disclosed in U.S. Pat. No. 6,121,503 (making plastic with an olefin product having a paraffin to olefin weight ratio less than or equal to 0.05), U.S. Pat. No. 6,187,983 (electromagnetic energy to reaction system), PCT WO 99/18055 publishes Apr. 15, 1999 (heavy hydrocarbon in the effluent stream fed to another reactor) PCT WO 01/60770 published Aug. 23, 2001 and U.S. patent application Ser. No. 09/627,634 filed Jul. 28, 2000 (high pressure), U.S. patent application Ser. No. 09/507,838 filed Feb. 22, 2000 (staged feedstock injection), and U.S. patent application Ser. No. 09/785,409 filed Feb. 16, 2001 (acetone co-fed), which are all herein fully incorporated by reference.

In another embodiment, olefin(s) produced are directed to, in one embodiment, one or more polymerization processes for producing various polyolefins. (See for example, U.S. patent application Ser. No. 09/615,376 filed Jul. 13, 2000 that is herein fully incorporated by reference.)

Polymerization processes include solution, gas phase, slurry phase and a high-pressure process, or a combination thereof. Particularly preferred is a gas phase or a slurry phase polymerization of one or more olefin(s) at least one of which is ethylene or propylene. Polymerization processes include those non-limiting examples described in the following: U.S. Pat. Nos. 4,543,399, 4,588,790, 5,028,670, 5,317,036, 5,352, 749, 5,405,922, 5,436,304, 5,453,471, 5,462,999, 5,616,661, 5,627,242, 5,665,818, 5,677,375, 5,668,228, 5,712,352 and 5,763,543 and EP-A-0 794 200, EP-A-0 802 202, EP-A2-0 891 990 and EP-B-0 634 421 describe gas phase polymerization processes; U.S. Pat. Nos. 3,248,179 and 4,613,484, 6,204,344, 6,239,235 and 6,281,300 describe slurry phase polymerization processes; U.S. Pat. Nos. 4,271,060, 5,001, 205, 5,236,998 and 5,589,555 describe solution phase polymerization processes; and U.S. Pat. Nos. 3,917,577, 4,175, 169, 4,935,397, and 6,127,497 describe high pressure polymerization processes; all of which are herein fully incorporated by reference.

These polymerization processes utilize a polymerization catalyst that can include any one or a combination of the molecular sieve catalysts discussed above, however, the preferred polymerization catalysts are those Ziegler-Natta, Phillips-type, metallocene, metallocene-type and advanced polymerization catalysts, and mixtures thereof. Non-limiting examples of polymerization catalysts are described in U.S. Pat. Nos. 3,258,455, 3,305,538, 3,364,190, 3,645,992, 4,076, 698, 4,115,639, 4,077,904 4,482,687, 4,564,605, 4,659,685, 4,721,763, 4,879,359, 4,960,741, 4,302,565, 4,302,566, 4,302,565, 4,302,566, 4,124,532, 4,302,565, 5,763,723, 4,871,705, 5,120,867, 5,324,800, 5,347,025, 5,384,299, 5,391,790, 5,408,017, 5,491,207, 5,455,366, 5,534,473, 5,539,124, 5,554,775, 5,621,126, 5,684,098, 5,693,730, 5,698,634, 5,710,297, 5,714,427, 5,728,641, 5,728,839, 5,753,577, 5,767,209, 5,770,753 and 5,770,664, 5,527,752, 5,747,406, 5,851,945 and 5,852,146, all of which are herein fully incorporated by reference.

In preferred embodiment, the present invention comprises a polymerizing process of one or more olefin(s) in the presence of a polymerization catalyst system in a polymerization reactor to produce one or more polymer products, wherein the one or more olefin(s) having been made by converting an alcohol, particularly methanol, using a zeolite or zeolite-type molecular sieve catalyst composition. The preferred polymerization process is a gas phase polymerization process and at least one of the olefins(s) is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kpag) to greater than about 1000 psig (3448 kPag), preferably in the range of from about 200 psig (1379 kpag) to about 500 psig (3448 kPag), and more preferably in the range of from about 250 psig (1724 kpag) to about 350 psig (2414 kpag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 Kg/hr), preferably greater than 35,000 lbs/hr (15,900 Kg/hr), more preferably greater than 50,000 lbs/hr (22,700 Kg/hr) and most preferably greater than 75,000 lbs/hr (29,000 Kg/hr).

The polymers produced by the polymerization processes described above include linear low density polyethylene, elastomers, plastomers, high density polyethylene, low density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene based polymers have a density in the range of from 0.86 g/cc to 0.97 g/cc, a weight average molecular weight to number average molecular weight (Mw/Mn) of greater than 1.5 to about 10 as measured by gel permeation chromatography, a melt index (I2) as measured by ASTM-D-1238-E in the range from 0.01 dg/min to 1000 dg/min, a melt index ratio (I21/I2) (I21 is measured by ASTM-D-1238-F) of from 10 to less than 25, alternatively a I21/I2 of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefins, numerous other olefin derived products are formed from the olefin(s) recovered any one of the processes described above, particularly the conversion processes, more particularly the GTO process or MTO process. These include, but are not limited to, aldehydes, alcohols, acetic acid, linear alpha olefins, vinyl acetate, ethylene dicholoride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes.

Use of Process Water in Catalyst Preparation

In another embodiment, the process water is used in the synthesis of molecular sieves, such as SAPO molecular sieves, to yield a highly crystalline, pure material having good catalytic performance for the conversion of methanol to light olefins. For example, the process water may be used in sieve synthesis or washing to prepare a molecular sieve.

Additionally or alternatively, the process water is used in the preparation of a formulated catalyst composition. For example, the process water may be used in the spray drying process and/or in catalyst extrusion to prepare extrudates.

This embodiment of the present invention will be better understood with reference to the following examples, which are intended to illustrate specific embodiments within the overall scope of the invention as claimed.

EXAMPLES 1-4

Example 1 is a control sample using demineralized water in the synthesis and final washing of EMM-2 (an intergrowth of SAPO-34 (AEI) and SAPO-18 (CHA)) molecular sieves. In each of Examples 2-4, process water from an oxygenate to olefin reaction system was used as the slurrying (gelling) agent and/or during final washing of the EMM-2 molecular sieves. The process water was derived from the bottoms stream of a condensate tower, e.g., the separation unit 46 shown in FIG. 2. The process water had a conductivity of about 600 μS/cm and contained the following trace elements, based on the total weight of the process water: Fe: 0.04 wppm; K: 0.03 wppm; Na: 211 wppm; Ca: 0.22 wppm; Cr: 0.02 wppm; Mg: 0.01 wppm; and Ni<0.01 wppm.

The characteristics of the molecular sieves synthesized in Examples 1-4 are provided in Table I, below:

TABLE I

| Molecular Sieve Synthesis Characteristics of Examples 1-4 | | | | | |
|---|---|---|---|---|---|
| Example No. | Gel Composition ($Si/Al_2$) | Gel T (° C.) | Crystallization T (° C.) | Slurrying Agent | Washing Agent |
| 1 (control) | 0.20 | 30 | 165 | Demineralized Water | Demineralized Water |
| 2 | 0.20 | 30 | 165 | Demineralized Water | Process Water |
| 3 | 0.11 | 10 | 165 | Process Water | Demineralized Water |
| 4 | 0.11 | 10 | 165 | Process Water | Process Water |

The so-synthesized molecular sieve was characterized by DIFFaX to determine the CHA/AEI ratio. DIFFaX is an X-ray diffraction calculational technique for determining the CHA/AEI ratio. The catalytic activity of each of the thus synthesized molecular sieves for converting methanol to light olefins was analyzed in a tubular microflow reactor, through well-known techniques. Prior to testing, the molecular sieves were calcined to remove the organic template (5 hours in $N_2$ followed by 3 hours in air at 650° C.). For each example, 20 mg of calcined molecular sieve was admixed with 60 mg of SiC as an inert. The admixture was added to a tubular microreactor and heated to 475° C. Methanol was passed through the microreactor at a WHSV of 100 $hr^{-1}$ and at a pressure of 25 psig (172 kPag). The catalytic performance of the molecular sieve was characterized by measuring: (a) the Cumulative Methanol Converted per Gram of Sieve (CMCPS, the amount of methanol converted normalized by the amount of sieve present); (b) the weight average prime olefin selectivity (POS); (c) the weight average selectivity of ethylene ($C_2^=$); (d) the weight average selectivity of propylene ($C_3^=$); (e) the weight average ratio of ethylene to propylene formed; (f) the weight average selectivity of methane ($C_1$); (g) the weight average selectivity of propane ($C_3^0$); (h) the weight average selectivity of $C_4$ compounds; (i) the weight average selectivity of $C_5^+$ compounds formed; and (0) the weight average selectivity of coke. These results are shown in Table II, below.

TABLE II

| Summary of Catalytic Activity of Examples 1-4 | | | | | | | | | | | |
|---|---|---|---|---|---|---|---|---|---|---|---|
| Ex. No. | Diffax CHA/AEI ratio | CMCPS (g/g sieve) | POS wt % | $C_2^=$ wt % | $C_3^=$ wt % | $C_2^=/C_3^=$ | $C_1$ wt % | $C_3^0$ wt % | $C_4$ wt % | $C_{5+}$ wt % | Coke wt % |
| 1 | 70/30 | 17.1 | 72.67 | 32.11 | 40.56 | 0.792 | 1.83 | 1.39 | 15.32 | 4.68 | 2.91 |
| 2 | 70/30 | 19.0 | 72.82 | 31.89 | 40.93 | 0.779 | 1.84 | 1.16 | 15.56 | 4.82 | 2.68 |
| 3 | 72/28 | 30.7 | 73.78 | 32.46 | 41.32 | 0.786 | 1.83 | 0.41 | 15.91 | 5.21 | 2.04 |
| 4 | 75/25 | 29.6 | 73.32 | 31.94 | 41.38 | 0.772 | 1.92 | 0.44 | 16.08 | 5.29 | 2.13 |

The data in Table II shows that OTO process water can be successfully used in the synthesis of EMM-2 molecular sieves: (i) without having a negative effect on catalyst performance; (ii) without a negative impact on the DIFFaX CHA/AEI ratio; and (iii) without impurities. Further, these experiments demonstrate that significant amounts of sodium can be present during the EMM-2 sieve synthesis.

Also, it is now expected that process water could not only be used in sieve synthesis and washing, but also in the preparation of the final catalyst. Thus, OTO process water could also be used in the spray drying process and in catalyst extrusion to prepare extrudates. It is also now expected that the use of OTO process water is not limited to EMM-2 synthesis but that OTO process water could be used in general for SAPO as well as zeolite synthesis and/or formulation/extrusion.

Use of Process Water in Other Reaction Processes

In another embodiment, the process water is used to produce chemicals by hydration of unsaturated hydrocarbons. Optionally, the hydration reaction comprises the hydration of acetylene to form acetaldehyde. Preferably, this reaction occurs at about 20 bar, about 200° C. and about a 5:1 molar ratio of water to acetylene. Alternatively, the hydration reaction comprises the hydration of ethylene to ethanol. This reaction preferably occurs at from about 40 bar to about 50 bar, at about 200° C. and at about a 2:1 molar ratio of water to ethylene. Alternatively, the hydration reaction comprises the hydration of propylene to form isopropyl alcohol, preferably in a trickle bed process utilizing resin catalyst at about 70 bar. Alternatively, the hydration reaction comprises the hydration of butene to sec-butanol, e.g., with sulfuric acid or trickle bed resin catalyst. Alternatively, the hydration reaction comprises the hydration of butadiene to methyl ethyl ketone (MEK) or butyraldehyde.

In another embodiment, process water from an OTO reaction system is utilized in the production of acetylene using well-known calcium carbide (CaC) processes. For a description of this process, see K. Weissermel, and H-J. Arpe, *Industrial Organic Chemistry*, Verlag Chemie, 1978, pp. 83-84. Alternatively, the OTO derived process water is used as cooling water in the well-known partial oxidation conversion of methane to acetylene. For a description of this process, see K. Weissermel, and H-J. Arpe, *Industrial Organic Chemistry*, Verlag Chemie, 1978, p. 86. The acetylene thus produced optionally is hydrated to acetaldehyde, again optionally using OTO derived process water.

In one embodiment, the OTO derived process water is directed to a steam cracking system. Acetylene production in steam cracking can be maximized, if desired, by increasing the severity of the steam cracking process. Thus, in one embodiment, the invention includes increasing the steam partial pressure, which should lead to an increased production of acetylene. That is, acetylene production can be improved with a greater steam partial pressure and/or at higher temperature in the steam cracking furnace. In one embodiment, the steam cracking system comprises a severe ethane steam cracker or a specially designed gasoil steam cracker. In this embodiment, the effluent stream formed in the steam cracking system optionally comprises at least about 10 weight percent acetylene and a substantial amount of ethylene. Optionally, a solvent, e.g., N-methylpyrrolidone or dimethylformamide, is used to extract the acetylene away from the ethylene and ethane in an acetylene recovery unit (ARU). Alternatively, the acetylene or acetylene/ethylene mixture is use as is.

The foregoing description of the invention including but not limited to drawings is intended to illustrate one or more embodiments of the invention and is non-limiting. While the invention has been illustrated an described herein in terms of the advantages, features, and applications disclosed, it will be apparent to a person of ordinary skill in the art that the invention can be used in other instances. Other modifications and improvements can be made without departing from the scope of the invention.

We claim:

1. A process for converting oxygenates to one or more olefin product streams, the process comprising the steps of:
   (a) optionally synthesizing a molecular sieve;
   (b) optionally combining the synthesized molecular sieve with a binder and optionally also with a matrix material to produce a formulated molecular sieve catalyst;
   (c) providing an oxygenate feed stream to an oxygenate to olefin reactor;
   (d) contacting the oxygenate feed stream in the oxygenate to olefin reactor with the formulated molecular sieve catalyst under conditions effective to produce an effluent stream comprising one or more olefins and byproduct water;
   (e) recovering and treating said one or more olefins in one or more olefin product streams, the step of recovering having a process water requirement;
   (f) recovering in a single-stage direct quench device the byproduct water from the effluent stream in the form of process quality water, which comprises:
      (v) about 1 wt. % or less metal ion salts;
      based upon the composition of the process quality water; and
   (g) supplying about 25 wt. % or more of the process water requirement from byproduct water, wherein the process water requirement is water that is consumed in the oxygenate to olefin process by at least one application in the process that consumes water without recovering the consumed water;
   wherein the process quality water is combined with the starting materials in the synthesis of molecular sieves, or in the preparation of a formulated catalyst composition.

2. The process of claim 1, wherein the effluent stream comprises from about 30 wt. % to about 70 wt. % water, based upon the composition of the effluent stream as it leaves the reactor.

3. The process of claim 1, wherein the effluent stream comprises from about 0.05 wt. % to about 5 wt. % alcohol based upon the composition of the effluent stream as the effluent stream leaves the reactor.

4. The process of claim 1, wherein the effluent stream comprises from about 0.01 wt. % to about 5 wt. % organic acids based upon the composition of the effluent stream as the effluent stream leaves the reactor.

5. The process of claim 1, wherein the effluent stream comprises about 5 wt. % or less aromatic compounds based upon the composition of the effluent stream as the effluent stream leaves the reactor.

6. The process of claim 1, wherein the effluent stream comprises about 0.3 wt. % or less nitrogen containing compounds, based upon the composition of the effluent stream as it leaves the reactor.

7. The process of claim 1, wherein the effluent stream comprises about 0.3 wt. % or less sulfur containing compounds, based upon the composition of the effluent stream as it leaves the reactor.

8. The process of claim 1, wherein the effluent stream comprises from about 0.3 wt. % or less halogen, based upon the composition of the effluent stream as it leaves the reactor.

9. The process of claim 1, wherein the step of (g) supplying, supplies 30 wt. % or more of the byproduct water.

10. The process of claim 1, wherein the step of (g) supplying, satisfies 30 wt. % or more of the water requirement from byproduct water.

11. The process of claim 1, wherein step (f) comprises quenching the effluent stream from the direct quench device to form a quenched effluent stream and a quench bottoms stream.

12. The process of claim 11, wherein the quench bottoms stream further comprises from about 0.05 wt. % to about 5 wt. % alcohol based upon the composition of the quench bottoms stream as the quench bottoms stream leaves the quench device.

13. The process of claim 11, wherein the quench bottoms stream has about 5 wt. % or less catalyst fines based upon the composition of the quench bottoms stream.

14. The process of claim 11, wherein the quench bottoms stream comprises from about 0.01 wt. % to about 5 wt. % organic acids, based upon the composition of the quench bottoms stream as it leaves the quench device.

15. The process of claim 11, wherein the quench bottoms stream further comprises about 5 wt. % or less aromatic compounds based upon the composition of the quench bottoms stream as the quench bottoms stream leaves the quench device.

16. The process of claim 11, wherein the quench bottoms stream further comprises about 0.1 wt. % or less nitrogen containing compounds, based upon the composition of the quench bottoms stream as it leaves the quench device.

17. The process of claim 11, wherein the quench bottoms stream comprises about 0.1 wt. % or less sulfur containing compounds, based upon the composition of the quench bottoms stream as it leaves the quench device.

18. The process of claim 11, wherein the quench bottoms stream comprises about 0.1 wt. % or less halogen containing compounds, based upon the composition of the quench bottoms stream as it leaves the quench device.

* * * * *

UNITED STATES PATENT AND TRADEMARK OFFICE
CERTIFICATE OF CORRECTION

PATENT NO. : 7,626,067 B2
APPLICATION NO. : 10/870185
DATED : December 1, 2009
INVENTOR(S) : Van Egmond et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 887 days.

Signed and Sealed this

Second Day of November, 2010

David J. Kappos
*Director of the United States Patent and Trademark Office*